(12) United States Patent
Noh et al.

(10) Patent No.: US 9,554,985 B2
(45) Date of Patent: Jan. 31, 2017

(54) AGENT FOR PROMOTING HAIR GROWTH AND METHOD FOR PREPARING SAME

(71) Applicant: KERATINT KOREA CO., LTD., Busan (KR)

(72) Inventors: Byung-Seung Noh, Gyeongsangnam-do (KR); Se-Eung Noh, Jeollabuk-do (KR)

(73) Assignee: KERATINT KOREA CO., LTD., Busan (KR)

( * ) Notice: Subject to any disclaimer, the term of this patent is extended or adjusted under 35 U.S.C. 154(b) by 56 days.

(21) Appl. No.: 14/404,769

(22) PCT Filed: Nov. 29, 2012

(86) PCT No.: PCT/KR2012/010263
§ 371 (c)(1),
(2) Date: Dec. 1, 2014

(87) PCT Pub. No.: WO2013/180358
PCT Pub. Date: Dec. 5, 2013

(65) Prior Publication Data
US 2015/0147415 A1 May 28, 2015

(30) Foreign Application Priority Data

May 29, 2012 (KR) ........................ 10-2012-0056608

(51) Int. Cl.
| | |
|---|---|
| *A61K 36/185* | (2006.01) |
| *A61K 36/254* | (2006.01) |
| *A61K 36/534* | (2006.01) |
| *A61K 36/484* | (2006.01) |
| *A61K 8/97* | (2006.01) |
| *A61Q 7/00* | (2006.01) |

(52) U.S. Cl.
CPC . *A61K 8/97* (2013.01); *A61Q 7/00* (2013.01); *A61K 2800/59* (2013.01)

(58) Field of Classification Search
None
See application file for complete search history.

(56) References Cited

FOREIGN PATENT DOCUMENTS

| | | |
|---|---|---|
| JP | 2010143862 | 7/2010 |
| KR | 1020060037206 | 3/2006 |
| KR | 20090095039 | 9/2009 |

OTHER PUBLICATIONS

Jadhav et al. (2009) Int. J. PharmTech Res. vol. 1, No. 3, pp. 454-467.*
Price (1999) NEJM vol. 341, No. 13, pp. 964-973.*

* cited by examiner

*Primary Examiner* — Chris R Tate
*Assistant Examiner* — Russell Fiebig
(74) *Attorney, Agent, or Firm* — IPLA P.A.; James E. Bame

(57) ABSTRACT

An agent for promoting hair growth and a preparation method for the same are provided. The method for preparing an agent for promoting hair growth that includes: (1) preparing an extract from eight medicinal herbs combined together at an optimal combination ratio to contain 50 to 70 wt. % of *Rumex japonicas* HOUTT, 3 to 6 wt. % of *Pleuropterus multiflorus*, 1 to 2 wt. % of *Radix Notoginseng*, 1 to 2 wt. % of safflower (*Carthamus tinctorius* L.), 1 to 2 wt. % of *Cnidium officinale*, 0.5 to 1 wt. % of *Mentha Arvensis* var. *Piperascens*, 0.5 to 1 wt. % of *Asarum sieboldii*, and 0.5 to 1 wt. % of *Glycyrrhiza uralensis* Fischer; and (2) adding 10 to 15 wt. % of a purified horse fat to the extract. The present invention exhibits the remarkable effects of promoting hair growth, preventing hair loss, and providing skin care functions through the treatment of the underlying diseases, such as kidney infection, heart problems and liver disorders, that are in direct and close relation to hair loss, and by promoting blood circulation and metabolic activity.

2 Claims, 5 Drawing Sheets

⟨ Before ⟩  ⟨ During treatment ⟩  ⟨ After ⟩
         (1 to 2 months)

Fig. 7

⟨Subject: male in 50s⟩

(a) Early stage   (b) After one month   (c) After two months

⟨Subject: male in 60s⟩

(a) Early stage   (b) After one month   (c) After two months

AGENT FOR PROMOTING HAIR GROWTH AND METHOD FOR PREPARING SAME

BACKGROUND

The present invention relates to an agent for promoting hair growth and a preparation method for the same. More particularly, the present invention relates to an agent for promoting hair growth and a preparation method for the same, where the agent for promoting hair growth contains an extract consisting of *Rumex japonicas* HOUTT, *Pleuropterus multiflorus, Radix Notoginseng*, safflower (*Carthamus tinctorius* L.), *Cnidium officinale, Mentha Arvensis* var. *Piperascens, Asarum sieboldii*, and *Glycyrrhiza uralensis* Fischer to promote hair growth and prevent production of premature gray hair and alopecia areata.

Hair loss, or alopecia, classified as alopecia areata, male pattern alopecia or female pattern alopecia, refers to an excessive hair-loss condition that results in baldness occurring where the hair is usually present.

Alopecia areata is a condition which hair is lost in coin-like round bald patches on the scalp due to inflammatory disease spread into hair follicles and, not infrequently, nails. Usually, the bald patches are easily distinguishable with obvious boundary and in most cases the hair loss can be quite sudden without any other symptom. The hair loss involves not only the scalp but also other areas of the body, including the beard, eyebrows, eyelashes, or the like. Based on the severity and the shape of the bald patches, the forms of alopecia areata include alopecia totalis and alopecia universalis. The hair loss that spreads to cover the entire scalp is called alopecia totalis. If it spreads over the entire body, the condition is called alopecia universalis. Alopecia totalis and alopecia universalis, sometimes become progressive to combine with each other and expand, frequently with the change of natural cure and recurrence.

Male pattern baldness mostly affects men, involves hair loss on the top and front of the head and a receding hairline, and, in the worse case, remains only a few hairs at the rear of the head.

Female pattern baldness has a similar pattern of hair loss to the male pattern baldness, excepting that even hair loss appears dominantly over the top and front of the head but less around the sides of the head.

There are various causes of alopecia: hair production disorder, hair breakage caused by endogenous factors, disheveled hair, abnormal hair growth cycle, destruction of hair follicles, and so forth. Some hair loss conditions that are diffuse may be caused by hair production disorder or hair breakage and possibly related with hereditary abnormalities. Some hair loss conditions caused by the abnormal hair growth cycle include telogen effluvium, anagen effluvium, alopecia areata, etc. Telogen effluvium can be triggered by endocrine disorder, drugs, or various physical and/or mental stresses. Anagen effluvium is associated with radiation therapy or anticancer drugs. Alopecia areata, although its causes are little well understood, is known as an autoimmune disease. Androgenic alopecia is triggered by androgenic hormones and hereditary factors and classified as local alopecia associated with hair production disorder. Other causes of alopecia include trichotillomania, trichophytia superficialis capillitii, etc.

Different forms of alopecia have different symptoms. Losing up to 100 hairs a day is normal, but shedding more than 50 to 60 hairs a day suggests the diagnosis of alopecia.

Alopecia areata mostly presents as a loss of hair in localized areas of the scalp or any other region of the body to leave round or fused bald patches or sometimes in the similar pattern of alopecia totalis (hair loss over the entire scalp) or alopecia universalis (hair loss over the entire body). With alopecia areata, the scalp appears normal and the affected hairs at the periphery of the lesion are 'exclamation point hairs' which are tapered towards the scalp end with thickening and broken in short length at the distal end. Gray hairs are not affected. In some cases, alopecia areata may accompany an autoimmune disease, such as thyroid disease, or malformation of nails (onychodystrophy).

Telogen effluvium involves a hair loss that occurs 2 to 4 months after a specific trigger such as endocrine disorder or drugs and usually decreases over several months as the hairs become restores from the resting phase to normal after the removal of the trigger. It takes around 6 to 12 months to have the hairs grow to some density.

Androgenic alopecia is a common form of hair loss in about 50 percent of both men and women, usually in their 30s or 40s and often in early adolescence. The region of hair loss starts from the forehead and gradually increases to cover the entire head. Men typically presents with hairline recession at both sides of the head and hair loss on the top of the head, while women normally does not have hairline recession but undergoes hair loss in the Christmas tree pattern.

The diagnosis and treatment of alopecia will now be described. The diagnosis of alopecia involves a dermatologist's checking the patient's medical history, an ocular inspection on the lesion, a hair pull test, a biopsy, a hair shaft inspection, and so forth. A dual diagnosis is also performed, for hypopituitarism, hypoadrenalism, hypoparathyroidism, and testicular feminization syndrome are alopecia-related diseases.

The treatment of alopecia such as alopecia areata presenting a localized bald patch includes intralesional steroid injection that involves steroids injected directly into a lesion at intervals of 4 to 6 weeks, or topical or oral administration of steroids. Patients with alopecia areata who does not respond to the other treatments or with extensive alopecia areata may benefit from the immunotherapy.

Androgenic alopecia can be treated with topical minoxidil therapy that involves using a 2% to 5% solution of minoxidil. Female patients with androgenic alopecia may benefit from the oral administration of birth control pills. Male patients with androgenic alopecia may take finasteride, in which case it is known that about 50 percent of the patients has an increase in the hair growth in one year of the finasteride treatment.

There have also been suggested other treatments, such as hair transplant as a surgical therapy, cleansing shampoo, an agent for promoting hair growth, and so forth. Especially, many patent documents from Korea and other countries disclose different agents for promoting hair growth that includes a blend of natural herbs and their preparation methods.

Although numerous known agents and methods for promoting hair growth have been introduced, there is no report that the patients' hair is dramatically promoted to regenerate and secure long-term prevention of hair loss. When patients with alopecia are treated with steroids through injection into the lesion or topical or oral administration of minoxidil or birth control pills for a long time, a few of them have gynecomastia and the diagnostic yield of prostate cancer is low according to the results of a 7-year clinical test on finasteride performed by FDA, but the incidence of high-grade prostate cancer highly malignant and aggressive increases. Moreover, it is well known that the medicines for treatment of alopecia do not accumulate in the body but are mostly excreted from the body in 24 hours. But, hair gradually begins to fall out 3 to 6 months after the patient stops taking the medicine. It is thus needed to take the medicine for such a long time as possible, still with a risk of side effects.

Accordingly, based on the various experiences and expertise of the applicant of the present invention as an international Chinese medical doctor and professor of traditional Chinese medicine at Henan University of Traditional Chinese Medicine in China, the present invention is to provide a novel agent for promoting hair growth and a preparation method for the same, where the agent for promoting hair growth includes, as an active ingredient, an extract mixture of horse fat and a medicinal herb material obtained according to the herbal treatment method by drying eight medicinal herbs having a curative effect to fundamentally cure the diseases directly and closely related to alopecia and skin ailments and also effects to promote hair growth, prevent hair loss and help skin care, among a number of medicinal herbs that grow naturally all over the world and do no harm to the human skin even after a long-term application.

SUMMARY OF THE INVENTION

It is therefore an object of the present invention to solve the problems as described above and, more specifically, to provide an agent for promoting hair growth and a preparation method for the same, where the agent for promoting hair growth contains an extract mixture obtained by optimally mixing a dried medicinal herb material including eight medicinal herbs consisting of *Rumex japonicas* HOUTT, *Pleuropterus multiflorus*, *Radix Notoginseng*, safflower (*Carthamus tinctorius* L.), *Cnidium officinale*, *Mentha Arvensis* var. *Piperascens*, *Asarum sieboldii*, and *Glycyrrhiza uralensis* Fischer and horse fat being close to a vegetable oil and containing 60% unsaturated fat at golden ratio, heating and ageing to achieve extraction for a defined period of time.

To accomplish the object of the present invention, there is provided a method for preparing an agent for promoting hair growth that includes:

(1) washing, cutting in a predetermined size and drying eight medicinal herbs consisting of *Rumex japonicas* HOUTT, *Pleuropterus multiflorus*, *Radix Notoginseng*, safflower (*Carthamus tinctorius* L.), *Cnidium officinale*, *Mentha Arvensis* var. *Piperascens*, *Asarum sieboldii*, and *Glycyrrhiza uralensis* Fischer and then mixing the eight medicinal herbs at an optimal weight percentage to prepare a herbal medicine material for promoting hair growth;

(2) adding the herbal medicine material together with 10 to 15 L of purified water in a 20-30 L herb medicine brewing pot and adjusting heat to perform a first decoction under pressure and temperature conditions of 2 kgf/cm$^2$ and 80° C. to 90° C. for 2 to 3 hours;

(3) letting the herb medicine brewing pot stand for about 2 to 3 hours after the first decoction until the pressure and temperature conditions in the herb medicine brewing pot become a zero point, heating up the herb medicine brewing pot again at 80° C. to 90° C. for 1 to 2 hours and then turning off the heat;

(4) keeping the herb medicine brewing pot filled with the herbal medicine material for promoting hair growth at a low temperature of 7° C. to 8° C. for 12 hours to perform a cold ageing;

(5) heating up the herb medicine brewing pot filled with the herbal medicine material for 2 to 3 hours to the pressure and temperature conditions of 2 kgf/cm$^2$ and 80° C. to 90° C. and then maintaining the heat for a predetermined period of time;

(6) obtaining an extract for promoting hair growth from the herbal medicine material contained in the herb medicine brewing pot through a 200-mesh filtration apparatus;

(7) adding the extract for promoting hair growth in a simmering pot heated at 90° C. to 100° C. and sufficiently evaporating water while stirring with a spatula to prevent sticking on the pot; and (8) adding the water-removed extract for promoting hair growth in an evaporator, adjusting the concentration of the extract until the extract has a sticky texture, adding a purified horse fat and adjusting heat to reheat up to 70° C. to 80° C. for 0.5 to 1 hour.

Preferably, the eight medicinal herbs are combined together at an optimal combination ratio to contain 50 to 70 wt. % of *Rumex japonicas* HOUTT, 3 to 6 wt. % of *Pleuropterus multiflorus*, 1 to 2 wt. % of *Radix Notoginseng*, 1 to 2 wt. % of safflower (*Carthamus tinctorius* L.), 1 to 2 wt. % of *Cnidium officinale*, 0.5 to 1 wt. % of *Mentha Arvensis* var. *Piperascens*, 0.5 to 1 wt. % of *Asarum sieboldii*, and 0.5 to 1 wt. % of *Glycyrrhiza uralensis* Fischer.

Preferably, the purified horse fat is added in an amount of 10 to 15 wt. %.

The agent for promoting hair growth and its preparation method according to the present invention has the effects as follows.

According to the present invention, using, as an active ingredient, an extract for promoting hair growth that is extracted from a mixture obtained by optimally mixing a herbal medicine material consisting of eight dried medicinal herbs of *Rumex japonicas* HOUTT, *Pleuropterus multiflorus*, *Radix Notoginseng*, safflower (*Carthamus tinctorius* L.), *Cnidium officinale*, *Mentha Arvensis* var. *Piperascens*, *Asarum sieboldii*, and *Glycyrrhiza uralensis* Fischer and horse fat containing unsaturated fat at an optimal combination ratio can benefit the following effects:

(1) The eight medicinal herbs growing naturally all over the world are herbal medicine materials themselves, so using an optimal mixture of the eight medicinal herbs at an optimal combination ratio according to the above-described Application of herbal medicines, the principles of Seven Consequences and Compatibility, can provide effects to fundamentally cure the kidney or liver troubles closely related to alopecia and skin problems, strengthen vigor of the body to promote hair growth and prevent hair loss and enhance the beauty of the skin such as by improving wrinkles.

(2) The eight medicinal herbs employed in the present invention, of which are human-friendly substances without toxicity, do no harm to the human body, promote blood circulation and metabolic activity to increase the immune function of the body, suppress the destruction of cell membranes and oxidization and inhibit melanin production to prevent scalp diseases such as scalp irritation, skin allergies, and skin problems, and suppress abrupt ageing of the body to extend the life span.

(3) The addition of purified horse fat that is close to a vegetable oil rich in unsaturated fats and vitamin E makes an oil layer with the horse fat penetrating into the scalp to prevent diffusion of charging and improve heat effect, thereby making it possible to supply nutrients sufficiently for the hair roots to promote hair growth and prevent hair loss and giving the skin whitening effect. Uniquely, the purified horse fat used in the present invention also enables long-term storage of the agent for promoting hair growth according to the present invention without any decomposition.

110: Eight medicinal herbs
120: Herbal medicine mixture
130: Extract for promoting hair growth
140: Purified horse fat
150: Evaporator
160: Hair growth promoting agent (Gel)

DETAILED DESCRIPTION OF THE INVENTION

Hereinafter, a detailed description will be given as to an agent for promoting hair growth and a preparation method for the same according to a preferred embodiment of the present invention with reference to the accompanying drawings.

It should be noted that the same reference numerals are used throughout the different drawings to designate the same or similar components. Further, in the description of the present invention, a detailed description of known functions and configurations incorporated herein will be omitted when it may make the subject matter of the present invention unclear.

Application of herbal medicines comprises compatibility, contraindications and cautions, and recommended dosage and administration. The compatibility is a critical factor in the application of herbal medicines and refers to the use of at least two selected herbal medicines in combination on the basis of the disease status, the efficacy and virtue of herbal medicines, and the usage of the herbal medicines.

The reasonableness of compatibility has a direct effect on the curative value of the herbal medicines.

The compatibility of herbs has been gradually developed from a sole prescription and involves the application of single-flavored herbs and the combinational relationship between the herbs as discovered from a long-term use of the herbs. The seven different patterns of compatibility are referred to as the "Seven Consequences".

1) Single application refers to using a herb alone; for example, using a ginseng root to replenish primordial Gi and a Scutellaria root to treat cough with blood from pulmonary tuberculosis.

2) Mutual reinforcement involves two or more ingredients with similar properties used in combination to reinforce each other's function through the synergy effect.

For example,
Gypsum+Anemarrhena asphodeloides Bunge
Bupleurum falcatum+Scutellaria Root
Anemarrhena asphodeloides Bunge+Phellodendron Bark
Ginseng+*Glycyrrhiza uralensis* Fischer Fischer
Angelica Gigas Root+*Cnidium officinale*
Nelumbinis Semen+Dioscoreae Rhizoma Root 3) Mutual assistance involves two ingredients with certain similar properties and functions used in combination to increase therapeutic effect: one acts as a main herb, the other as an assistant.

For example,
Astragalus Root+Poria cocos Wolf
Artemisiae Argyi Herb+Cyperus rotundus Linne Root
Anthriscus sylvestris (L.) Hof+Pinelliae Tuber 4) Mutual inhibition occurs when two ingredients are used together: one reduces or dispels the therapeutic function of the other.

For example,
Coptis Rhizome+Ginger
Saposhnikovia Root+Zingiberis Rhizoma
Ginseng+Radish Semen
White Paeoniae radix+Dendrobium monliforme
*Cnidium officinale*+Coptis Rhizome
Mgnolia Bark+Alismatis Rhizoma 5) Mutual restraint is meant to use two ingredients together: toxic reaction or side effects from one can be weakened or neutralized by the other.

For example,
Pinelliae Tuber+Ginger: Ginger reduces or eliminates stimulation of Pinelliae tuber on the throat.
Asari Radix+talc
Liriopis Tuber+Saphora Root 6) Mutual antagonism involves two ingredients used in combination to cause toxic reactions or side effects.

For example,
Rehmanniae Radix+Raphanus sativus Linne (Radish seed)
Picrorrhozae Rhizoma+Scrophularia buergeriana
*Glycyrrhiza uralensis* Fischer+Euphorbia pekinensis 7) Mutual detoxification refers to using two ingredients in combination: one can weaken or neutralize the toxicity or side effects of the other. Mutual restraint and mutual detoxification are the same concept explained from different perspectives.

For example,
Saposhnikovia Root+Aconitum carmichaeli Debeaux
Angelica Dahurica Root+Realgar
Japanese Felt Fern Leaf Prosia lingua+Cinnabaris
Pinelliae Tuber+Ginger Accordingly, the agent for promoting hair growth and its preparation method according to a preferred embodiment of the present invention contains an extract as an active ingredient obtained by mixing eight dried medicinal herbs including 50 to 70 wt. % of *Rumex japonicas* HOUTT, 3 to 6 wt. % of *Pleuropterus multiflorus*, 1 to 2 wt. % of *Radix Notoginseng*, 1 to 2 wt. % of safflower (*Carthamus tinctorius* L.), 1 to 2 wt. % of *Cnidium officinale*, 0.5 to 1 wt. % of *Mentha Arvensis* var. *Piperascens*, 0.5 to 1 wt. % of *Asarum sieboldii*, and 0.5 to 1 wt. % of *Glycyrrhiza uralensis* Fischer, and 10 to 15 wt. % of horse fat containing 60 percent of unsaturated fat and being close to a vegetable oil together at an optimal "gold combination ratio" according to the above-described Application of herbal medicines, the principles of Seven Consequences and Compatibility, thereby exerting remarkable effects not just to fundamentally treat kidney or liver diseases closely related to alopecia, promote hair growth and prevent production of premature gray hair and alopecia areata but also to enhance the beauty of the skin, such as improving skin problems, wrinkles, etc.

Figure 1:
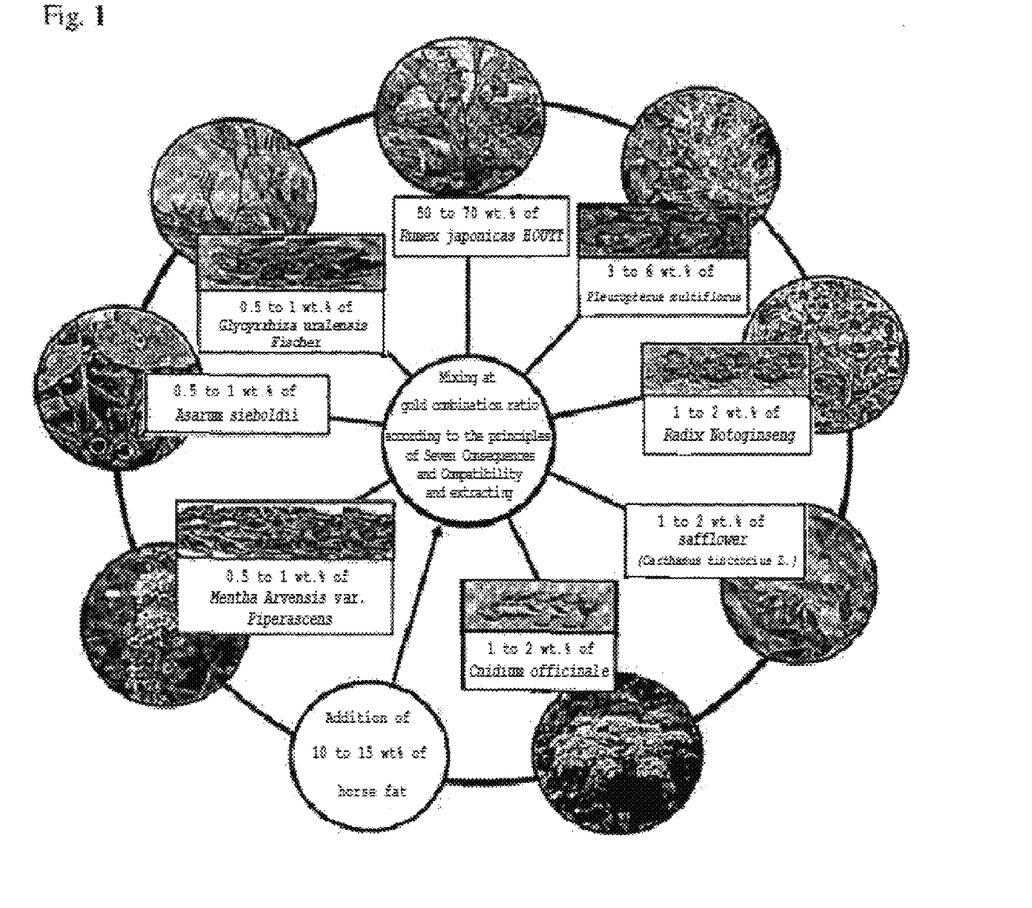
FIG. 1 is an illustration showing a combination of eight medicinal herbs and horse fat in the agent for promoting hair growth and its preparation method according to a preferred embodiment of the present invention.

Referring to FIG. 1, a detailed description will be given as to the features, principal ingredients, and efficacies of the herbal medicine material of eight dried medicinal herbs and horse fat rich in unsaturated fats and vitamin E as used in optimal combination in the agent for promoting hair growth and it's preparation method according to a preferred embodiment of the present invention.

[1] *Rumex japonicas* HOUTT, contained at an amount of 50 to 70 wt. % in the extract mixture (or composition) in the agent for promoting hair growth and its preparation method according to an embodiment of the present invention, serves to prevent scalp diseases (e.g., dandruff, scalp irritations, etc.) skin allergies and skin problems and improve kidney disease that is in direct relation to hair loss.

More specifically, the *Rumex japonicas* HOUTT, a perennial herb plant belonging to the family Polygonaceae, is widely distributed in a little damp places, such as sunny field, farmland, vacant lot, etc., growing to a height of 40 to 100 cm with thick and yellow roots, thin and erect stems, oblong leaves to 25 cm long and 4 to 10 cm wide in an alternate leaf arrangement. Young leaves are edible or used in the treatment of skin diseases and the root is used as stomachic.

As cited in SANRIM KYONGJAE, *Rumex japonicas* HOUTT contains oxalic acid, which is what makes it inedible in raw but edible only after parboiled in water, and is distributed mainly in Korea, Japan, Sakhalin, Kamchatka, etc.

*Rumex japonicas* HOUTT is especially effective in treating skin diseases, like boil, furuncle, etc. For example, the juice of the raw root or the powder of the root mixed with vinegar can be applied to a lesion with leukoplakia, scalp disease, ringworm, eczema, eczema in pubic region, itchy skin, and obstinate scabies. The root decoction is good to stop uterine hemorrhage, nose bleeding, etc. and also to treat nausea, diarrhea, indigestion, acute and chronic enteritis, constipation, lymphadenitis, tonsillitis, etc.

Further, a long-term administration of *Rumex japonicas* HOUTT is excellent in effects to make intestines and blood clean and skin texture smooth, eliminate inflammation and kill various germs, so it can be used in the treatment of all inflammatory diseases and cancers, such as gastritis, stomach ulcer, stomach cancer, etc.

*Rumex japonicas* HOUTT is also effective in relieving fever and promoting induction of perspiration, consequently with a therapeutic effect for cold, pulmonary tuberculosis, cough, and bronchitis, and remarkably useful to treat a kidney infection or difficult urination that has a direct influence on the hair loss.

[2] *Pleuropterus multiflorus*, contained at an amount of 3 to 6 wt. % in the extract mixture (or composition) in the agent for promoting hair growth and its preparation method according to an embodiment of the present invention, aids the functions of the kidneys and liver that are in close relation to hair loss and skin problems, making gray hair darker, improving premature gray hair, alopecia areata, etc. and strengthening bones, sinews and bone marrow to make life expectancy longer.

More specifically, *Pleuropterus multiflorus*, a perennial climbing herb plant belonging to the family Polygonaceae, has the root containing, as principal ingredients, about 1.8% oxymethylanthraquinone derivatives (e.g., chrysophanol, chrysophanol anthrone, emodinmonometalester, physcion, derivatives thereof, etc.), 45.2% starch, 3.1% crude fat, 3.7% lecithin, and 2% tetrahydroxystilbene and glucoside, and other water-insoluble substances.

On the other hand, Donguibogam (Principles and Practice of Eastern Medicine) states that *Pleuropterus multiflorus* can replenish primordial Gi, darken gray hair after a long-term administration, with therapeutic effects to improve premature gray hair and alopecia areata, and strengthen bones and sinews to help extension of the life expectancy.

Further, *Pleuropterus multiflorus* exerts excellent therapeutic effects on the chronic diseases, such as the diseases related to the circulatory system and anemia and other diseases accounting for the disorder of the blood circulation and recovers the failing health caused by a nervous breakdown or ageing.

All the hair of the body is bound up with the kidneys and liver. Hence, the kidneys in poor health lead to frequent hair loss and the deteriorated functions of the liver cause immediate fatigue and skin problems. *Pleuropterus multiflorus* can be a good herbal medicine for protecting the functions of the kidneys and liver.

In addition, *Pleuropterus multiflorus* can be used in combination with steamed *Rehmanniae glutinosa* root, raw *Rehmanniae glutinosa* root and *Angelica Gigas* Root to treat the menstrual irregularity that occurs with profuse menstruation, irregular menstrual period or dark menstrual blood.

Further, *Pleuropterus multiflorus*, when used in combination with *Viscum Album* Var. *Coloratum, Eucommiae Cortex* and *Dipsaci Radix*, can strengthen the spine and joints and improve the body strength of patients who have a weak constitution or poor physical strength after a long sickness.

[3] *Radix Notoginseng*, contained at an amount of 1 to 2 wt. % in the extract mixture (or composition) in the agent for promoting hair growth and its preparation method according to an embodiment of the present invention, dilates blood vessels to raise the elasticity of the blood vessels, lowers the levels of fat and cholesterol in the blood to increase nutrient supply for the skin, and also inhibits production of melanin pigments involving in the skin whitening reaction to strengthen the elasticity of the skin and make the skin clean and smooth, thereby exerting a skin care effect to reduce the wrinkles on the skin.

More specifically, the *Radix Notoginseng* is a very critical herbal medicine in the haemostatic process applied to all the forms of bleeding in and out of the body. The *Radix Notoginseng* makes the blood flow smoothly and eliminates extravasated blood, so it can be used to treat all kinds of bleeding, stomachache due to extravasated blood, abscess, birth pain, postpartum bleeding, etc.

Further, the *Radix Notoginseng* is effective to relieve swelling and pain and thus used in the treatment of swelling and pain caused by a contused wound or a fracture, boils, furuncles, or the like.

[4] Safflower, contained at an amount of 1 to 2 wt. % in the extract mixture (or composition) in the agent for promoting hair growth and its preparation method according to an embodiment of the present invention, enhances the immune function of the body and prevents destruction of cell membranes to suppress the progress of ageing.

More specifically, the safflower is a perennial herb plant 40 to 100 cm tall has globular flower heads on the tip of the stem normally in June and July with the color turning from yellow to red and produces fruits in July and August.

On the other hand, the contents of platinum and other principal nutrient ingredients in the safflower are presented in Table 1.

TABLE 1

Platinum and Principal Nutrients Contained in Safflower

| Symbol | Ingredient | Functions | (Unit: ppm) Content |
|---|---|---|---|
| Pt | Platinum | Anticancer, bone production | 3.8 |
| Fe | Iron | Blood formation | 10 |
| Ca | Calcium | Major ingredient of bone | 1000 |
| Mg | Magnesium | Nerve stability, glycolytic enzyme | 100 |
| Mn | Manganese | Bone formation, enzyme synthesis | 10 |
| Na | Sodium | Physiological function | 100 |
| Si | Silicon | Bone growth | 10 |
| Al | Aluminum | Metabolic activity | 100 |
| Sr | Strontium | Calcium absorption | 1 |
| K | Potassium | Improving blood pressure, muscle and long-term fatigue | 1000 |
| B | Boron | Boron metabolic activity | 1 |
| Ba | Barium | Metabolic activity | 10 |
| P | Phosphor | Bone, nucleic acid Linoleic acid, cholesterol, lipids | 1000 |

Platinum is a metal that is originally of a high value in the aspects of precious metal, accessories, ornaments or industry and has recently become important as a material for anticancer drugs. As can be seen from Table 1, however, the platinum contained in the safflower has significant characteristics different from those of the normal metal platinum.

In other words, though the metal platinum can be a fatal poison to human or other animals, the organic platinum contained in the safflower is excellent in the anticancer function and remarkably effective to cure fractions or osteoporosis and help extension of the life expectancy.

The organic platinum is also useful in the treatment of incurable diseases without any toxicity or side effects. In particular, the safflower that grows wild in Korea, Nepal or is considerably rich in organic platinum.

The safflower seed is one of the three wonder drugs including wild ginseng and bamboo salt and widely used to treat incurable diseases. The safflower seed contains 15 to 35% safflower oil and has linoleic acid and glyceride as principal ingredients effective to prevent and treat obesity and arteriosclerosis (hardening of the arteries). The safflower seed also contains up to 90 ml of vitamin E that enhances the immune function and prevents destruction of cell membranes to prevent the progress of ageing.

The fatty acid composition of the safflower oil is made up of 74 to 77% linoleic acid, 13 to 14% oleic acid, 6.5 to 9.7% palmitic acid, 1.3 to 2.3% stearic acid, and 0.1 to 1.0% linolenic acid.

In this regard, the linoleic acid is an unsaturated fatty acid (i.e., a fatty acid that has a molecular structure with a double bond, a triple bond, or a quadruple bond unlike a saturated fatty acid) and also called "essential fatty acid" including linoleic acid or arachidonic acid, because it cannot be produced in human body. The linoleic acid, also referred to as vitamin F and in the liquid state at the room temperature, can be found a lot mostly in vegetable oils such as safflower oil, soybean oil, rapeseed oil, etc.

[5] *Cnidium officinale*, contained at an amount of 1 to 2 wt. % in the extract mixture (or composition) in the agent for promoting hair growth and its preparation method according to an embodiment of the present invention, is a representative herbal medicine used to make blood and Gi flow smoothly and thus good to improve headache, birth pain, sedation and nourishing of the blood and tonicity. Especially, *Cnidium officinale* cleans the fuzz out of the head, improves extravasated blood and inhibits activation of the stimulating hormone for melanin-producing cells, melanocytes, to prevent pigmentation and thus provide a skin whitening effect.

More specifically, *Cnidium officinale* is a perennial herb plant belonging to the family Apiaceae with a little bit spicy flavor and warm nature.

Donguibogam (Principles and Practice of Eastern Medicine) cites that "*Cnidium officinale* is indispensable for treating headache and thus necessarily used for the pains in the top of the head and brain". In other words, *Cnidium officinale* improves various symptoms caused by bad blood circulation in the body, such as headache, dizziness, irregular menstruation, menstrual pain, amenorrhea, stomachache, etc. Further, *Cnidium officinale* has a good therapeutic effect on the pains in association with abnormal blood stagnation due to an external injury or a contused wound. In addition, *Cnidium officinale* contains nutrient substances to become the components of blood and thus can be used as a drug for nourishing the blood in the case of anemia after pregnancy.

Therefore, *Cnidium officinale* dilates the blood vessels and prevent blood coagulation to make the blood circulation normal, thereby preventing obesity and adult diseases, such as arteriosclerosis, hyperlipidemia, etc., and cerebral infarction caused by blocked blood vessels and exerting a remarkable efficacy for women with menstrual headache.

[6] *Mentha Arvensis* var. *Piperascens*, contained at an amount of 0.5 to 1 wt. % in the extract mixture (or composition) in the agent for promoting hair growth and its preparation method according to an embodiment of the present invention, has a skin soothing and curing function, relieves muscle spasm, improves skin elasticity, kills germs, accelerates blood circulation, offers cooling sensation for the skin, and alleviates acne and skin irritation caused by sunlight.

More specifically, *Mentha Arvensis* var. *Piperascens*, a perennial herb plant belonging to the family Lamiaceae, is commonly named "Gubaka", "Yasikyang" or "Eohyangcho" and has leaves and stems contain, as principal ingredients, menthol, isomenthol, camphene, limonene, manganese, vitamin A, vitamin C, essential oil, etc. In particular, the essential oil functions to stimulate cerebral cortex and myelencephalon, induce perspiration and promote blood circulation, providing refreshing feeling in the mouth with a spicy and cool flavor.

The efficacies of *Mentha Arvensis* var. *Piperascens* include alleviation of a fever, anti-inflammation, stomach strengthening, stimulation of bile secretion, increasing secretion of mucus in the respiration track, dilation of capillary vessels, stimulant action on the central nervous system, uterine stimulant function, and curing boils. *Mentha Arvensis* var. *Piperascens* is also used in the treatment of indigestion, throat infection, tonsillitis, skin irritations, stomachache, diarrhea, nausea, headache, toothache, cold, furuncle, sore throat, inflamed eyes, etc. In addition, the folk medicine considers that the ingredients of *Mentha Arvensis* var. *Piperascens* can increase the male's vitality, cure neurological disorders and relieve a shack fever and fatigue.

[7] *Asarum sieboldii* is contained at an amount of 0.5 to 1 wt. % in the extract mixture (or composition) in the agent for promoting hair growth and its preparation method according to an embodiment of the present invention. *Asarum sieboldii* is a plain wild-ginger plant (*Asicasarum Heterotropoides* F. *Maekawa* var *mansshuricumf, maekawa*) or a wild-ginger plant (*Asicasarum sieboli* F. *Maekawa*), belonging to the family Aristolochiaceae, with thin roots having a unique smell that makes the tongue numb with spicy flavor and warm properties and has an anticancer function, a respiratory depression function on the liver cells, and an antispasmodic function.

For the physiological effects, *Asarum sieboldii* contains methyleugenol, safrole, and others, including asaryl, asaryl ketone, canole, pinene, flavonoid, and its hay has aristolochic acid and catecholamine. Further, trans-aconitic acid is contained at an amount of 3 to 11%.

The efficacies of *Asarum sieboldii* are provided to treat headache, neuralgia, backache, toothache, muscle ache, cold, chronic bronchitis, extravasated blood, hepatitis, rheumatoid arthritis, eye pain, menstruation stop, irritation, quadriplegia, apoplexy, phlegm, diuresis, sinus infection, rhinitis, chronic cough, asthma, nasal congestion, sweating, stomatitis, stomachache, shivering fits, pantalgia, repressed annoyance, runny nose, and birth pain, and have a function of sedation, immunosuppression, anti-allergy, and anti-germ.

[8] *Glycyrrhiza uralensis* Fischer, contained at an amount of 0.5 to 1 wt. % in the extract mixture (or composition) in the agent for promoting hair growth and its preparation method according to an embodiment of the present invention, neutralizes the other drug's functions, does hepatic detoxification to restore the functions of the liver, and especially inhibits occurrence of digestive ulcers using its ingredients, such as liquidritin, liquiritigenin, etc., thereby preventing hair loss.

In addition, *Glycyrrhiza uralensis* Fischer is excellent in promoting the syntheses of collagen and hyarulonnic acid and inhibiting production of melanin pigments to effectively improve skin elasticity and skin wrinkles.

More specifically, *Glycyrrhiza uralensis* Fischer is a perennial herb plant in the family of legume 30 to 80 cm tall, with a lignified base, thin and red-colored bark, and desirably with an upright and long branchy stem and a sweet flavor.

The principal ingredients of *Glycyrrhiza uralensis* Fischer are glysyrihizic acid, glabridin, saponaretin, licuracid as a kind of flavonoid, flavonoid, tripene-based saponin, etc. Regarding the efficacies, *Glycyrrhiza uralensis* Fischer has tranquil nature, neutralizes the toxicity of all drugs, gives a sweet flavor without toxicity and combines with a toxic substance to provide a detoxification function, thereby restoring the functions of the liver and exerting a good therapeutic effect in the treatment of drug addiction, infection, hives, dermatitis, eczema, etc.

In particular, among the principal ingredients of *Glycyrrhiza uralensis* Fischer, the glysyrihizic acid, collected from the root of *Glycyrrhiza uralensis* Fischer, is 30 to 50 times as sweet as sugar, making it possible to use *Glycyrrhiza uralensis* Fischer to prepare an artificial sweetener, and effective in inhibiting occurrence of cancer and tumor, reducing the cholesterol level to improve hardening of the arteries, and protecting the liver.

In addition, the glabridin has an antioxidant effect and an inhibitory effect on the production of melanin pigments, and the flavonoid has an anticancer function due to its strong antioxidant effect.

[9] Horse fat, contained at an amount of 10 to 15 wt. % in the extract mixture (or composition) in the agent for promoting hair growth and its preparation method according to an embodiment of the present invention, is rich in unsaturated fats and vitamin E (wheat germ oil), which is what makes the skin high in absorbability and water retention capacity, to effectively promote hair growth, prevent hair loss, improve skin wrinkles and protect the agent for promoting hair growth according to the present invention from going rancid even when it is stored for a long time.

The horse fat is a fat extracted from the adipose tissue of a horse and contains, as principal ingredients, about 40% saturated fat and 60% unsaturated fat, which is made up of 7.3% of palmitoleic acid, 34.8% of oleic acid, 14.2% linoleic acid, 0.9% linolenic acid, etc. This makes the horse fat closer to a vegetable oil rather than a fat from animals.

As Chinese traditional texts of materia medica, "Renowned Doctor's Specific Records" and "Bencao Kangmu", state that the horse fat promotes hair grow, cures chapped hands and feet and helps blood circulation, the horse fat has long been widely used as a remedy for burn or atopic dermatitis in the Asian areas such as Japan, etc.

The unsaturated fatty acids contained in the horse fat have efficacies to form cell membranes in the body, eliminate cholesterol, provides better use feelings on the skin than saturated fatty acids, and exhibits high levels of absorbability and water retention capacity to offer a skin protection function, a cell regeneration promoting function, a UV-screening function, and an antibacterial function.

The reason that the horse fat has such efficacies lies in the fact that the horse fact can penetrate deep into the skin pores. A microscopic observation on the molecule of the horse fat shows that strong bonding and separation are repeated in the molecule.

As the human skin has minutely uneven surface as well as pores that keep a tiny amount of air remaining in the subcutaneous tissue, the horse fat applied to the skin can penetrate deep into the skin to the extent that even the air remaining in the pores becomes expelled from the pores.

A general fat, when applied to the skin, causes surface tension on the surface of the skin and keeps the air stuck on the skin, so it cannot penetrate into the skin because of the air remaining on the skin. In contrast, the horse fat can readily penetrate into the skin tissue due to its high fluidity.

Further, the horse fat that penetrates into the subcutaneous tissue to the depth of 1 mm cannot just capture the germs from the outside through a wound such as a cut, etc. within the skin oil to bring the activity of cells to a stop but also inhibit the invasion of external germs into the skin, thereby with functions to prevent bacterial infection and cure a wound.

In addition, the horse fat is much similar in the compositional ingredients to the human fat, so it can penetrate into the subcutaneous tissue and become a nutrient, which is a human-friendly substance having no harm to the skin when absorbed into the blood, thereby promoting blood circulation and accelerating the metabolic activity.

Furthermore, the horse fat when applied onto the scalp in combination with massage can penetrate into the scalp to form an oil film, which prevents diffusion of charging and improve the heat effect. This enables it to sufficiently nourish the hair roots, leading to promotion of hair growth and prevention of hair loss.

Hereinafter, the agent for promoting hair growth and the preparation method for the same will be described in detail.

Example 1

Figure 2:
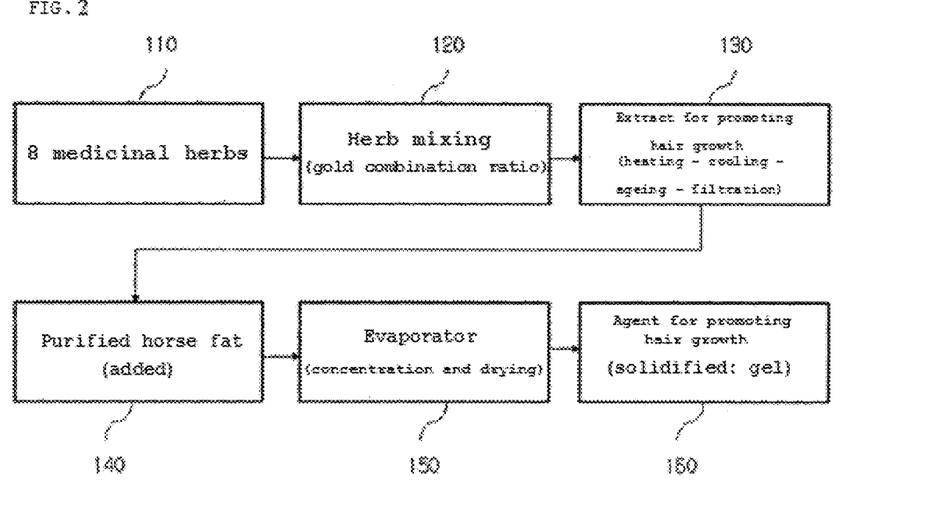
FIG. 2 is a block diagram showing the technical mechanism of the agent for promoting hair growth according to a preferred embodiment of the present invention.

Referring to FIGS. 1 and 2, the agent for promoting hair growth according to a preferred embodiment of the present invention will be described as follows.

Eight medicinal herbs 110 commercially available, including 50 to 70 wt. % of *Rumex japonicas* HOUTT, 3 to 6 wt. % of *Pleuropterus multiflorus*, 1 to 2 wt. % of *Radix Notoginseng*, 1 to 2 wt. % of safflower (*Carthamus tinctorius* L.), 1 to 2 wt. % of *Cnidium officinale*, 0.5 to 1 wt. % of *Mentha Arvensis* var. *Piperascens*, 0.5 to 1 wt. % of

*Asarum sieboldii*, and 0.5 to 1 wt. % of *Glycyrrhiza uralensis* Fischer, are dried and mixed together to prepare a herbal extract 130.

In this regard, the eight medicinal herbs are washed, chopped in a defined size and then dried to prepare an herbal medicine material, which includes the eight medicinal herbs optimally combined together at a "gold combination ratio" in terms of weight percentage (wt. %) according to the above-described Application of herbal medicines, the principles of Seven Consequences and Compatibility.

Further, the herbal extract 130 that contains the active (or therapeutic) ingredients for promoting hair growth can be prepared by heating the herbal medicine material obtained by drying the mixture of the eight medicinal herbs at 80 to 90 C for a predetermined period of time and then passing the herbal medicine material through a 200-mesh filtration apparatus.

In this regard, the method of producing the herbal extract for promoting hair growth will be specifically described in further detail in association with the after-mentioned preparation method for the agent for promoting hair growth.

In the embodiment of the present invention, 10 to 15 wt. % of a purified horse fat 140 is added to the herbal extract 130, which is then concentrated with an evaporator 150 for a predetermined period of time and then dried out to form a gel 160.

The object of adding 10 to 15 wt. % of the purified horse fat to the herbal extract of the herbal medicine material made up of an optimal combination of eight dried medicinal herbs is to protect the herbal extract from going rancid when it is transferred into a gel and stored in a container for a long time. The antiseptic effect of the horse fat results from the richness of unsaturated fatty acids and vitamin E (wheat germ oil) in the horse fat.

Further, the horse fat that is much similar in the compositional ingredients to the human fat can penetrate into the subcutaneous tissue and act as a nutrient, which is a human-friendly substance having no harm to the skin when absorbed into the blood and yet promoting blood circulation and accelerating the metabolic activity.

Furthermore, the horse fat applied onto the scalp while used in combination with massage can penetrate deep into the pores of the skin so as to expel the air from the pores. At the same time, the horse fat penetrating into the scalp forms an oil film to prevent diffusion of charging and improve the heat effect. This enables it to sufficiently nourish the hair roots, making it possible to sufficiently nourish the hair roots and help promotion of hair growth and prevention of hair loss.

Example 2

The method for preparing an agent for promoting hair growth according to a preferred embodiment of the present invention will be described with reference to FIGS. 3, 4 and 5.

Figure 3:
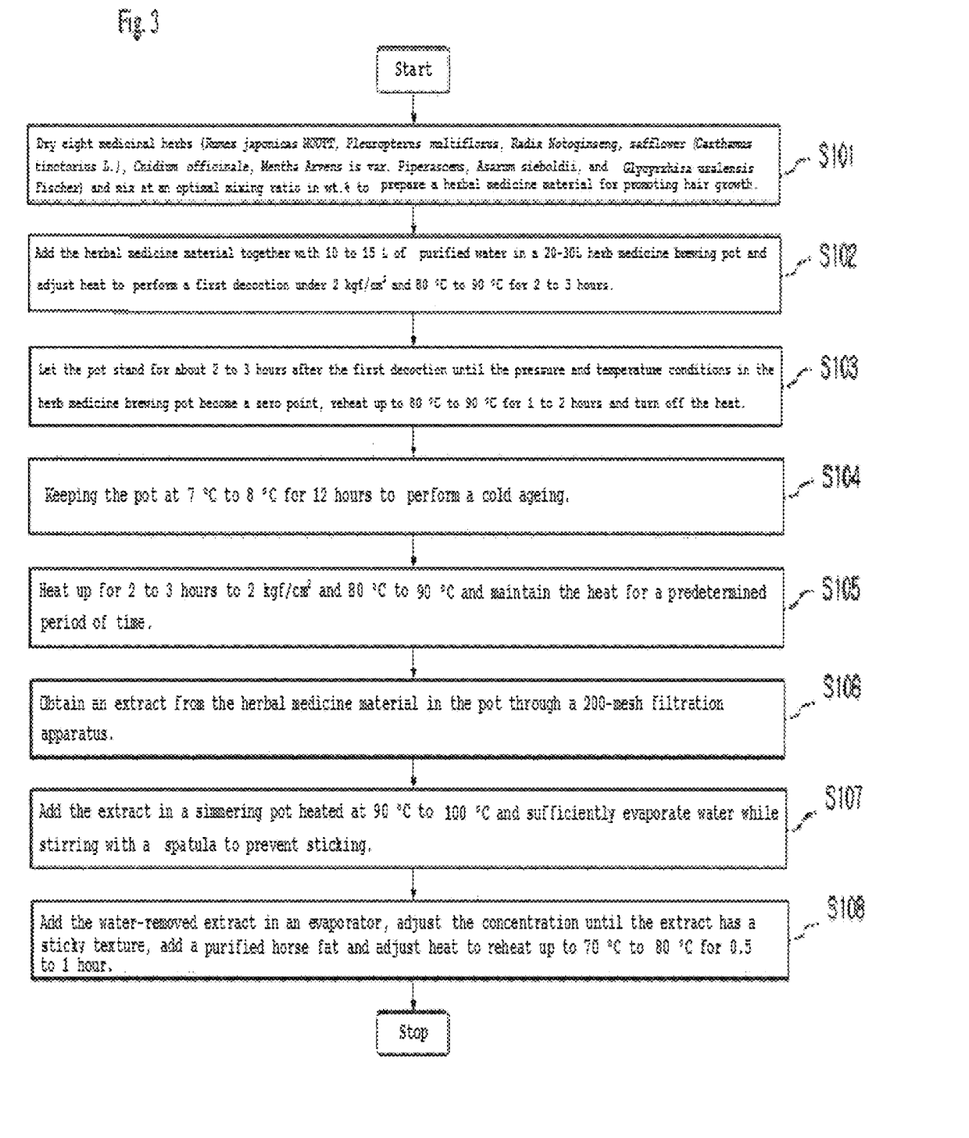
FIG. 3 is a flow chart showing a method for preparing an agent for promoting hair growth according to a preferred embodiment of the present invention.

Referring to FIG. 3, eight medicinal herbs commercially available, including *Rumex japonicas* HOUTT, *Pleuropterus multiflorus, Radix Notoginseng*, safflower (*Carthamus tinctorius* L.), *Cnidium officinale, Mentha Arvensis* var. *Piperascens, Asarum sieboldii*, and *Glycyrrhiza uralensis* Fischer, are washed, chopped in a predetermined size, dried out and then optimally combined together at a "gold combination ratio" in terms of weight percentage (wt. %) according to the above-described Application of herbal medicines, the principles of Seven Consequences and Compatibility to prepare a herbal medicine material for promoting hair growth, in a first step S101.

Figure 4:
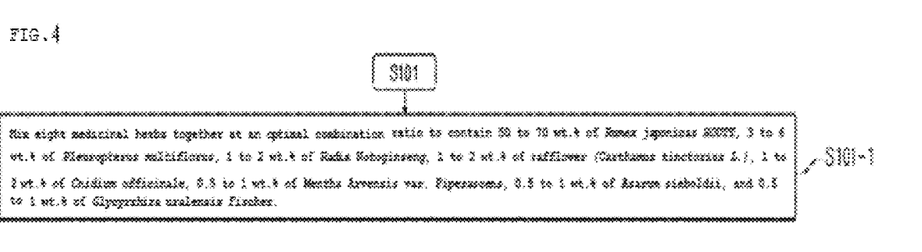
FIGS. 4 and 5 are flow charts showing another process of the method for preparing an agent for promoting hair growth as shown in FIG. 3.

Referring to FIG. 4, the composition of the herbal medicine material obtained from the eight dried medicinal herbs is made up of 50 to 70 wt. % of *Rumex japonicas* HOUTT, 3 to 6 wt. % of *Pleuropterus multiflorus*, 1 to 2 wt. % of *Radix Notoginseng*, 1 to 2 wt. % of safflower (*Carthamus tinctorius* L.), 1 to 2 wt. % of *Cnidium officinale*, 0.5 to 1 wt. % of *Mentha Arvensis* var. *Piperascens*, 0.5 to 1 wt. % of *Asarum sieboldii*, and 0.5 to 1 wt. % of *Glycyrrhiza uralensis* Fischer at such a "gold combination ratio", in step S101-1.

The characteristics, principal ingredients and efficacies of the eight medicinal herbs are as defined above and not described any more.

Particularly, the herbal medicine obtained from the eight dried medicinal herbs according to an embodiment of the present invention is characterized by the fact that all the eight medicinal herbs are carefully selected from a number of medicinal herbs not only to fundamentally cure the diseases in association with the kidney, liver or blood circulation systems directly or closely related to the cause of alopecia but also to sufficiently have a good effect on the skin by promotion of hair growth or prevention of hair loss.

Subsequently, the herbal medicine material obtained from the eight dried medicinal herbs combined together at an optimal combination ratio (in wt. %) and 10 to 15 L of purified water are put in a 20-30 L herb medicine brewing pot and then heated up to perform a first decoction under pressure and temperature conditions of 2 kgf/cm$^2$ and 80° C. to 90° C. for 2 to 3 hours, in a second step 102.

In the second step, the object of the first decoction performed by heating at 80 to 90° C. for 2 to 3 hours rather than at 100° C. is to sufficiently soak the herbal medicine material of the eight medicinal herbs with the purified water and let it steep to extract medicinal properties.

After the first decoction, the herb medicine brewing pot is stood for about 2 to 3 hours until the pressure and temperature conditions in the herb medicine brewing pot become a zero point, heated again up to 80° C. to 90° C. for 1 to 2 hours and then cooled down with the heat off, in a third step S103.

Subsequent to the third step, the herb medicine brewing pot filled with the herbal medicine material for promoting hair growth is kept at a low temperature of 7° C. to 8° C. for 12 hours to perform a cold ageing, in a forth step S104.

After the cold ageing, the herb medicine brewing pot filled with the herbal medicine material is heated up for 2 to 3 hours to the pressure and temperature conditions of 2 kgf/cm$^2$ and 80° C. to 90° C. and then maintaining the heat for a predetermined period of time, in a fifth step S105.

The object of repeating the third, fourth and fifth steps is to make up for the insufficient decoction in the second step and sufficiently combine the respective medicinal ingredients from the eight medicinal herbs together.

In other words, these steps are important procedures to extract all the medicinal ingredients for promoting hair growth from the herbal medicine material of the eight dried medicinal herbs optimally mixed together at a gold combination ratio according to the Application of herbal medicines, the principles of Seven Consequences and Compatibility, and to sufficiently combine all the effective medicinal ingredients by ageing at low temperature. This is a unique technique (or secret method) that is hard to contrive even by those skilled in the art.

After the fifth step, the herbal medicine material with the medicinal ingredients of the eight medicinal herbs sufficiently extracted in the evaporator is subjected to filtration in a 200-mesh filtration apparatus to obtain an extract for promoting hair growth, in a sixth step S106.

The object of using the 200-mesh filtration apparatus is to filter out the sludge that is the impurities of the extract for promoting hair growth generated in the second to fifth steps.

The extract for promoting hair growth as obtained from the filtration apparatus is put in a simmering pot heated at 90° C. to 100° C. and sufficiently stirred with a spatula to evaporate water and prevent sticking on the pot, in a seventh step S107.

The water-removed extract for promoting hair growth is put in an evaporator and heated up to adjust the concentration until the extract has a sticky texture and, after adding a purified horse fat, it is reheated up to 70° C. to 80° C. for 0.5 to 1 hour, in an eighth step S108.

Figure 5:
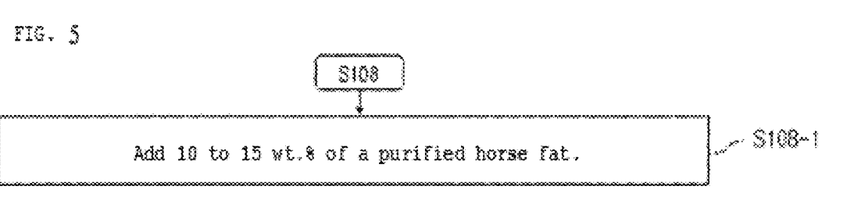

Referring to FIG. 5, the amount of the purified horse fat added to the extract is 10 to 15 wt. %, in S108-1.

Hereinafter, a detailed description will be given as to the experimental results of the toxicity testing on the gel for promoting hair growth (cosmetic sample) according to a preferred embodiment of the present invention that is performed by the Korea Testing & Research Institute.

TABLE 2

Toxicity Testing on Agent for Promoting Hair Growth
Sample: Cosmetic sample
Test results

| Item | Unit | Sample | Result | Test method |
|---|---|---|---|---|
| pH | — | — | 4.7 | No. 2009-158 - Ministry of Food and Drug Safety |
| Pb | mg/kg | — | Not detected | No. 2009-158 - Ministry of Food and Drug Safety |
| As | mg/kg | — | Not detected | No. 2009-158 - Ministry of Food and Drug Safety |
| Mercury | mg/kg | — | Not detected | No. 2009-158 - Ministry of Food and Drug Safety |
| Methanol | % (v/v) | — | Not detected | No. 2009-158 - Ministry of Food and Drug Safety |
| Methylparaffin | mg/kg | — | Not detected | Cosmetic composition limit analysis guideline 2010 |
| Ethylparaffin | mg/kg | — | Not detected | Cosmetic composition limit analysis guideline 2010 |
| Propylparaffin | mg/kg | — | Not detected | Cosmetic composition limit analysis guideline 2010 |
| DEHP | mg/kg | — | Not detected | Cosmetic hazardous substance analysis guideline 2010 |
| DEP | mg/kg | — | Not detected | US EPA 8061A 1996 (GC/MS) |
| DBP | mg/kg | — | Not detected | Cosmetic hazardous substance analysis guideline 2010 |
| BBP | mg/kg | — | Not detected | Cosmetic hazardous substance analysis guideline 2010 |

- Method Detection Limit (MDL) -
Pb: 2 mg/kg
As: 1 mg/kg
Bis(2-ethylhexyl)phthalate (DEHP): 5 mg/kg
Diethylphthalate (DEP): 5 mg/kg
Dibutylphthalate (EBP): 5 mg/kg
Benzylbutylphthalate (BBP): 5 mg/kg
Methanol: 0.025% (v/v)
Ethyl paraben: 5 mg/kg
Propyl paraben: 5 mg/kg
Butyl paraben: 5 mg/kg
Hg: 0.05 mg/kg According to the experimental results, the agent for promoting hair growth [solidified (gel type) cosmetic sample] that is comprised of eight medicinal herbs and a purified horse fat rich in unsaturated fatty acids and vitamin E according a preferred embodiment of the present invention has a pH of 4.7 that means it is nontoxic, doing no harm to the human body. The reason of this result is that the eight medicinal herbs, i.e., *Rumex japonicas* HOUTT, *Pleuropterus multiflorus, Radix Notoginseng*, safflower (*Carthamus tinctorius* L.), *Cnidium officinale, Mentha Arvensis* var. *Piperascens, Asarum sieboldii*, and *Glycyrrhiza uralensis* Fischer, are natural themselves and that the horse fat is a human-friendly substance closer to a vegetable oil rather than an animal fat.

Figure 6:
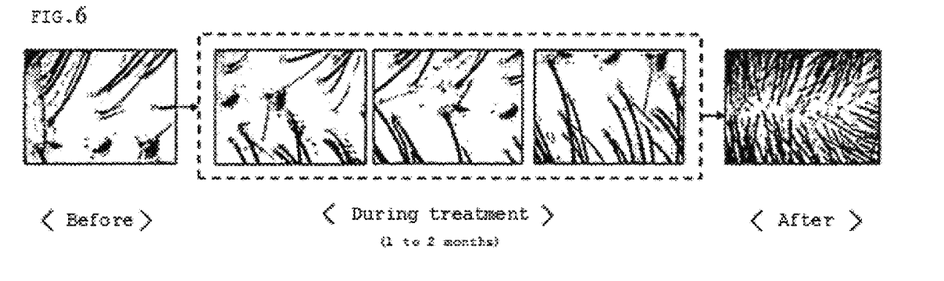
FIG. 6 is a photograph showing the Balmers hair growth test (BHT) in association with a clinical test on the agent for promoting hair growth and its preparation method according to a preferred embodiment of the present invention.
Figure 7:
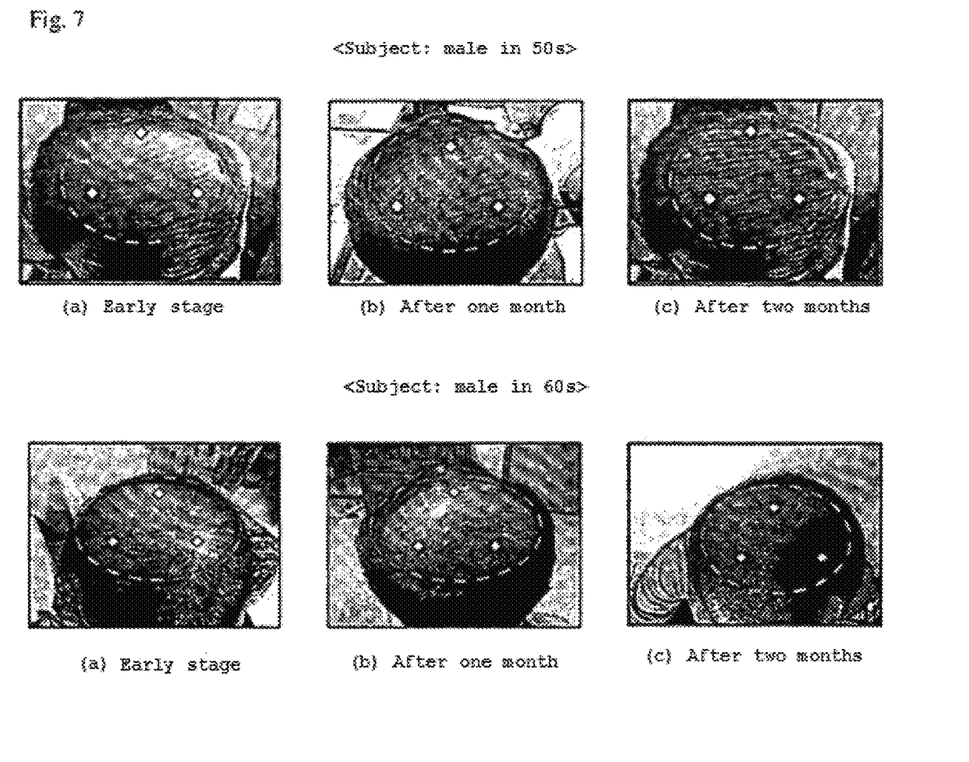
FIG. 7 is a photograph of a subject participating in the clinical test in association with the Balmers hair growth test of FIG. 6.

Reference will now be made to FIGS. 6 and 7 to describe 'an exemplary clinical test' on the agent for promoting hair growth (gel type cosmetic sample) according to a preferred embodiment of the present invention in further detail.

Referring to FIG. 6, the hair growth testing method according to the clinical test of the present invention is the 'Balmers hair growth test (BHT)', which is a test method that involves checking the hair count in the pore through photo interpretation before, during and after the hair growth treatment and comparing the hair count before the hair growth treatment with that after the hair growth treatment to evaluate the severity of hair loss.

Clinical Test Example 1

Referring to FIG. 7, in the clinical test on the agent for promoting hair growth according to an embodiment of the present invention, three bald-headed males in their 40s, 50s and 60s, respectively, are subjected to daily applications of the agent on a completely bald spot of the scalp for 2 months, 2 to 3 times a day. The hair photos (for the subjects in their 50s and 60s other than the subject in his 40s) after the treatment are compared with the hair photos before the treatment to check the similar progress, the hair growth progress, and the hair loss progress. The results are presented in Table 3.

In this regard, the reason that the hair photos of the subject in his 40s are excluded from FIG. 7 is that the hair photos of the subject in his 40s substantially have no difference from those of the subject in his 50s.

TABLE 3

Clinical Test Results on Hair Growth

| Sample | Similar progress | Hair growth progress | Hair loss progress | Subject |
|---|---|---|---|---|
| Gel cosmetic | ±1 | +3 | | Male in his 40s |
| Gel cosmetic | ±1 | +3 | | Male in his 50s |
| Gel cosmetic | ±1 | +2 | | Male in his 60s |

* ±1: Similar progress
* +2, +3: Hair growth promoted
* −2, −3: Severe hair loss
* Occupation of the subject in his 40s: office worker
* Occupation of the subject in his 50s: principal at special-education school
* Occupation of the subject in his 60s: Chinese medical doctor and professor As can be seen from Table 3 and FIG. 7, the hair loss differs in severity from subject to subject before the clinical test and shows a similar progress in the early stage of the clinical test. In about 2 weeks of the clinical test, the hair loss stops and hair growth begins. In one to two months, all the subjects undergo hair growth. As indicated by the yellow triangle sign in the red dotted line of FIG. 7, the hair loss almost disappears in two months of the clinical test, while the hair growth progress of the subject in his 60s on the center of the heat has a little difference from that of the subjects in their 40s and 50s. The subject in his 60s has a minor difference in the blood circulation or metabolic activity from the subjects in their 40s and 50s, yet with no significant difference in the severity of stress from the occupation. In conclusion, it is demonstrated that the extract comprised of a herbal medicine material obtained from the eight dried medicinal herbs, i.e., *Rumex japonicas* HOUTT, *Pleuropterus multiflorus, Radix Notoginseng,* safflower (*Carthamus tinctorius* L.), *Cnidium officinale, Mentha Arvensis* var. *Piperascens, Asarum sieboldii,* and *Glycyrrhiza uralensis* Fischer, and a purified horse fat rich in unsaturated fatty acids and vitamin E is a composition that exerts good effects not just to fundamentally cure the kidney infection, heart ailments and liver problems closely related to alopecia but also to strengthen vigor of the body, promote hair growth and prevent hair loss.

Clinical Test Example 2

In order to evaluate the agent for providing skin care effects and promoting hair growth according to a preferred embodiment of the present invention in regards to the skin care effects (i.e., skin whitening and wrinkle improving effects), the subjects of the clinical test of Table 3 are subjected to daily applications of the agent on the skin for 2 months, 2 to 3 times a day. Then, a viscometer is used to evaluate the skin improving effects, such as skin whitening effect caused by inhibition of melanin production, water content, the depth of wrinkles caused by dead skin cells and oil, spots on the skin, the size of pores, etc. For the sake of private protection, the facial photos of the subjects are not shown and the evaluation results are presented in Table 4.

TABLE 4

Clinical Test Results on Hair Growth Promotion

| Sample | Similar progress | Effective | Ineffective | Subject |
|---|---|---|---|---|
| Gel cosmetic | ±1 | +3 | | Male in his 40s |
| Gel cosmetic | ±1 | +2 | | Male in his 50s |
| Gel cosmetic | ±1 | +2 | | Male in his 60s |

* ±1: Similar progress
* +2, +3: Skin improved
* −2, −3: Skin not improved
* Occupation of the subject in his 40s: office worker
* Occupation of the subject in his 50s: principal at special-education school
* Occupation of the subject in his 60s: Chinese medical doctor and professor As can be seen from Table 4, the progress of skin improvement appears similar in all the three subjects in the early stage of the clinical test. In about 2 to 3 weeks of the clinical test, the skin begins to get a shiny complexion and becomes partly removed of spots, freckles, facial blemishes, etc. Further, in one to two months, all the subjects begin to benefit from the minimized pores and inhibition of melanin production to have the facial spots fade away and partly improved wrinkles. The skin improving effect appears more slowly in the subjects in their 50s and 60s than in the subject in his 40s. The reason is that the subjects in their 50s and 60s are slower in the blood circulation and metabolic activity than the subject in his 40s. Further, such a difference in the skin improving effect results from the skin retention capacity and skin ageing due to the ageing of the body rather than the severity of stress from the occupation. In conclusion, it is demonstrated that the extract comprised of a herbal medicine material obtained from the eight dried medicinal herbs, i.e., *Rumex japonicas* HOUTT, *Pleuropterus multiflorus, Radix Notoginseng,* safflower (*Carthamus tinctorius* L.), *Cnidium officinale, Mentha Arvensis* var. *Piperascens, Asarum sieboldii,* and *Glycyrrhiza uralensis* Fischer, and a purified horse fat rich in unsaturated fatty acids and vitamin E is a composition excellent in the skin care effects, because it inhibits production of melanin pigments, forms cell membranes in the body, eliminates cholesterol, protects the skin with high absorbability and water retention capacity, and promotes skin regeneration.

Hereinafter, a detailed description will be given as to the functions of the agent for promoting hair growth and the preparation method for the same according to a preferred embodiment of the present invention.

According to the embodiment of the present invention, an optimal "gold combination ratio" according to the above-described Application of herbal medicines, the principles of Seven Consequences and Compatibility is applied to prepare a composition of eight medicinal herbs made up of 50 to 70 wt. % of *Rumex japonicas* HOUTT, 3 to 6 wt. % of *Pleuropterus multiflorus,* to 2 wt. % of *Radix Notoginseng,* 1 to 2 wt. % of safflower (*Carthamus tinctorius* L.), 1 to 2 wt. % of *Cnidium officinale,* 0.5 to 1 wt. % of *Mentha Arvensis* var. *Piperascens,* 0.5 to 1 wt. % of *Asarum sieboldii,* and 0.5 to 1 wt. % of *Glycyrrhiza uralensis* Fischer and a horse fat containing 60% unsaturated fatty acids and being closer to a vegetable oil. The composition is subjected to a heat control to the defined pressure and temperature conditions and then a cold ageing to extract active ingredients of the herbal medicine material having a hair growth promoting effect and a skin care effect, so that it can exert good effects to fundamentally cure the kidney infection, heart ailments and liver problems closely related to alopecia, enhance blood circulation and metabolic activity to promote hair growth and prevent hair loss, and inhibit production of melanin pigments to provide a good skin care effect.

The foregoing description of a preferred embodiment of the invention has been presented for purposes of illustration and description. It is not intended to be exhaustive or to limit the invention to the precise form disclosed, and obviously many modifications and variations are possible in light of the above teaching. The embodiment was chosen and described in order to best explain the principles of the invention and its practical application to thereby enable others skilled in the art to best utilize the invention in various embodiments and with various modifications as are suited to the particular use contemplated. The scope of the present invention is not limited to the specific embodiments disclosed as the best modes planned to realize the present invention but includes all the embodiments according to the claims of the present invention.

The present invention relates to an agent for promoting hair growth and a preparation method for the same and, more particularly, to an agent for promoting hair growth and a preparation method for the same, which agent for promoting hair growth contains an extract consisting of *Rumex japonicas* HOUTT, *Pleuropterus multiflorus, Radix Notoginseng,* safflower (*Carthamus tinctorius* L.), *Cnidium officinale, Mentha Arvensis* var. *Piperascens, Asarum sieboldii,* and *Glycyrrhiza uralensis* Fischer to promote hair growth and prevent production of premature gray hair and alopecia areata.

What is claimed is:
1. A method for preparing a hair-growth promoting composition, comprising the steps of:
  (a) washing and drying herbs consisting of *Rumex japonicas* HOUTT, *Pleuropterus multiflorus, Radix Notogin-*

*seng*, safflower (*Carhtamus tinctorius* L.), *Cnidium officinale, Mentha Arvensis* var. *Piperascens, Asarum sieboldii* and *Glycyrrhiza uralensis* Fischer;

(b) mixing the washed and dried herbs in the following weight percentage ratio to obtain an herbal medicine material:

50 to 70 wt. % of *Rumex japonicas* HOUTT,
3 to 6 wt. % of *Pleuropterus multiflorus,*
1 to 2 wt. % of *Radix Notoginseng,*
1 to 2 wt. % of safflower (*Carhtamus tinctorius* L.),
1 to 2 wt. % of, *Cnidium officinale,*
0.5 to 1 wt. % of *Mentha Arvensis* var. *Piperascens,*
0.5 to 1 wt. % of *Asarum sieboldii,* and
0.5 to 1 wt. % of *Glycyrrhiza uralensis* Fischer;

(c) combining the herbal medicine material with 10 L to 15 L of purified water in a 20 L-30 L brewing pot and heating the brewing pot to perform a decoction under pressure and temperature conditions of 2 kgf/cm$^2$ and 80 to 90° C. for 2 to 3 hours;

(d) removing the brewing pot from the heat and letting the pot stand for about 2 to 3 hours;

(e) reheating the brewing pot to 80 to 90° C. for 1 to 2 hours;

(f) cooling the brewing pot to a temperature of 7 to 8° C. for 12 hours to perform a cold aging;

(g) reheating the brewing pot under pressure and temperature conditions of 2 kgf/cm$^2$ and 80 to 90° C. for 2 to 3 hours;

(h) filtering the herbal medicine material produced in step (g) through a 200-mesh filtration apparatus to obtain an extract;

(i) adding the extract in a pot of simmering water heated to 90 to 100° C., and evaporating the water while stirring to prevent the extract from sticking on the pot, to obtain a water-removed extract;

(j) adding the water-removed extract to an evaporator and drying the water-removed extract to produce a sticky-textured extract; and (k) adding purified horse fat to the sticky-textured extract to obtain a horse fat-containing extract, and (l) heating the horse fat-containing extract to 70 to 80° C. for 0.5 to 1 hour, to obtain said hair-growth promoting composition.

2. The method as claimed in claim 1, wherein the purified horse fat is added in an amount of 10 to 15 wt. %.

* * * * *